(12) United States Patent
Enejder

(10) Patent No.: US 6,510,330 B1
(45) Date of Patent: Jan. 21, 2003

(54) METHOD AND DEVICE FOR MEASURING BLOOD PARAMETERS

(75) Inventor: Annika Enejder, Lund (SE)

(73) Assignee: Gambro AB (SE)

( * ) Notice: Subject to any disclaimer, the term of this patent is extended or adjusted under 35 U.S.C. 154(b) by 0 days.

(21) Appl. No.: 09/856,765

(22) PCT Filed: Nov. 26, 1999

(86) PCT No.: PCT/SE99/02219

§ 371 (c)(1),
(2), (4) Date: Aug. 17, 2001

(87) PCT Pub. No.: WO00/33053

PCT Pub. Date: Jun. 8, 2000

(30) Foreign Application Priority Data

Nov. 30, 1998 (SE) ................................. 9804142

(51) Int. Cl.[7] ................................. A61B 5/50
(52) U.S. Cl. ......................... 600/322; 356/39
(58) Field of Search ................ 600/310, 322, 600/326, 328; 356/39

(56) References Cited

U.S. PATENT DOCUMENTS 4,745,279 A * 5/1988 Karkar et al. ................ 356/40
4,810,090 A    3/1989 Boucher et al. ............. 356/39
5,351,686 A   10/1994 Steuer et al.
5,385,539 A * 1/1995 Maynard ................... 600/322
5,601,080 A    2/1997 Oppenheimer
6,144,444 A * 11/2000 Haworth et al. ............ 600/322

FOREIGN PATENT DOCUMENTS

| EP | 0 467 804 B1 | 10/1995 |
| EP | 0 720 013 A2 | 7/1996 |
| EP | 0 800 074 A1 | 10/1997 |
| EP | 0 818 682 A2 | 1/1998 |
| WO | 94/08237 | 4/1994 |
| WO | 95/04266 | 2/1995 |

* cited by examiner

*Primary Examiner*—Eric F. Winakur
(74) *Attorney, Agent, or Firm*—Lerner, David, Littenberg, Krumholz & Mentlik, LLP

(57) ABSTRACT

Methods are disclosed for analysing the concentration of red blood cells in a flow of blood including flowing the blood through a cuvette, directing a light through the flow of blood, measuring light transmitted through the flow of blood to obtain a transmitted signal, measuring scattered light at a predetermined angle with respect to the direct transmission path through the flow of blood to obtain a scattered signal, and providing a ratio signal comprising the ratio between the scattered signal and the transmitted signal. Apparatus for analysing the concentration of red blood cells is also disclosed.

15 Claims, 4 Drawing Sheets

METHOD AND DEVICE FOR MEASURING BLOOD PARAMETERS

FIELD OF THE INVENTION

The present invention relates to a method and apparatus for measuring blood parameters. More particularly, the present invention relates to providing an optical signal proportional to total hematocrit or a concentration of red cells in blood. Still more particularly, the present invention relates to continuous measurement of the vascular blood volume during dialysis.

BACKGROUND OF THE INVENTION

Many optical sensors for the measurement of whole blood are designed for measuring the light transmission or reflection properties of blood, see, for example, International Application Nos. WO 94/08237 and WO 95/04266; European Patent Nos. 467,804, 800,074 and 818,682; and U.S. Pat. No. 5,351,686.

These measurements often fail to take into account the scattering properties of blood. The omission of this information results in data which is distorted by the light scattering of blood and consequently by properties such as the size, shape and orientation of the cells. The two latter properties are of particular significance when conducting measurements on flowing blood.

A more extensive measurement procedure is required in order to obtain results with minimal contribution of the scattering properties, like an assessment of the angular distribution of the light transmission, as described, for example, in U.S. Pat. No. 5,601,080, by recording the change in transmission at more than one wavelength, as described, for example, U.S. Pat. No. 4,810,090, or at varying sample thickness.

Another drawback with previously known measurement methods for deducing the hematocrit or hemoglobin is that the transmission signal has an exponential relationship with hematocrit or total hemoglobin. This means that the accuracy of the derived results are highly dependent on the quality of the calibration routine used. Moreover, the relationship is dependent on the oxygen saturation level of the blood and the osmolarity. Finally, and also of great importance, is the fact that the relationship is dependent on the flow rate of the blood in a complex manner, making it difficult to correct for the flow rate.

Patients suffering from end stage renal disease are regularly exposed to dialysis, essentially for removing waste products from the blood, balancing electrolytes, supplying buffer and removing excess water. During the removal of excess water, water is removed from the contents of the blood vessels, resulting in a decreased blood volume. The removal is balanced by vascular refilling from the surrounding tissue. However, if the blood volume is caused to decrease too much and too rapidly, the patient may suffer various symptomatic complications, such as hypotension, cramps, nausea and headache.

By measuring the concentration of red blood cells in the blood, a change of the blood volume can be estimated and an excessive reduction of the blood volume may be detected.

One object of the present invention is to provide an optical measurement method and apparatus for measurement of whole blood, which are robust and rugged, and which provide an output signal which is inherently essentially proportional to the concentration of red blood cells.

Another object of the present invention is to provide an optical measurement method and apparatus suitable for measurement of flowing whole blood.

A further object of the present invention is to provide an optical measurement method and apparatus having an increased sensitivity.

A still further object of the present invention is to provide an optical measurement method and apparatus suitable for use as a blood volume sensor during dialysis.

SUMMARY OF THE INVENTION

In accordance with the present invention, these and other objects have now been realized by the invention of a method for analyzing the concentration of red blood cells in a flow of blood comprising flowing the blood through a cuvette, directing a light along a direct transmission path through the flow of blood in the cuvette, measuring light transmitted through the flow of blood along the direct transmission path to obtain a transmitted signal, measuring scattered light at a predetermined angle with respect to the direct transmission path to obtain a scattered signal, and providing a ratio signal comprising the ratio between the scattered signal and the transmitted signal. Preferably, the predetermined angle is about 90°.

In accordance with one embodiment of the method of the present invention, the predetermined angle is between 70° and 110°, and preferably between 80° and 100°.

In accordance with another embodiment of the method of the present invention, the method includes directing the light from a light emitting member, measuring the light transmitted along the direct transmission path by means of a first light sensitive member, and measuring the scattered light by means of a second light sensitive member. In a preferred embodiment, the method includes surrounding at least a portion of the cuvette with light absorbing material in order to increase the sensitivity of the ratio signal. Preferably, the method includes emitting light having a restricted emission angle by means of the light emitting member.

In accordance with one embodiment of the method of present invention, the method includes activating the light emitting member in a pulsed mode.

In accordance with the present invention, these and other objects have also been realized by the invention of apparatus for analyzing the concentration of red blood cells in a flow of blood comprising a cuvette for the flow of blood, a light emitting member for directing a light along a direct transmission path through the flow of blood in the cuvette, a first light sensitive member for measuring light transmitted through the flow of blood along the direct transmission path to obtain a transmitted signal, a second light sensitive member for measuring scattered light at a predetermined angle with respect to the direct transmission path to obtain a scattered signal, and calculation means for providing a ratio signal comprising the ratio between the scattered signal and the transmitted signal. Preferably, the predetermined angle is about 90°.

In accordance with one embodiment of the apparatus of the present invention, the predetermined angle is between 70° and 110°, and preferably between 80° and 100°.

In accordance with one embodiment of the apparatus of the present invention, the apparatus includes light absorbing material surrounding at least a portion of the cuvette. Preferably, the light emitting member has a restricted emission angle.

In accordance with another embodiment of the apparatus of the present invention, the light emitting member is driven in a pulsed mode.

According to the present invention, it has been observed that both the transmitted signal as well as the side scattered signal have information essential for the evaluation of the red blood cell concentration in blood. Both signals decrease at increasing concentration, and the relationships are non-linear. The signals are dependent on oxygen saturation level, osmolarity and have a complex dependency on blood flow rate.

However, it has also been found, according to the present invention, that the ratio between the perpendicular scattered signal and the transmitted signal is essentially proportional to the red cell concentration, i.e. there is a linear relationship between the ratio signal and the red cell concentration. The ratio signal has, moreover, only a small dependency on the oxygen saturation level, osmolarity and blood flow rate.

Thus, according to the present invention, there is provided a method and apparatus for providing a signal proportional to a concentration of red cells in blood, total hemoglobin or hematocrit, comprising: flowing blood through a cuvette; exposing the flowing blood to light passing along a straight transmission path through the blood in the cuvette; measuring light transmitted along the transmission path to obtain a transmitted signal; measuring scattered light at an angle perpendicular to the transmission path to obtain a scattered signal; and forming a ratio signal which is the ratio between the scattered signal and the transmitted signal. The sensitivity may be increased by adapting light absorbing material at areas surrounding the cuvette or parts thereof.

BRIEF DESCRIPTION OF THE DRAWINGS

Further objects, features and advantages of the present invention appear from the following detailed description, which, in turn, makes reference to the drawings, in which.

DETAILED DESCRIPTION

Figure 1:
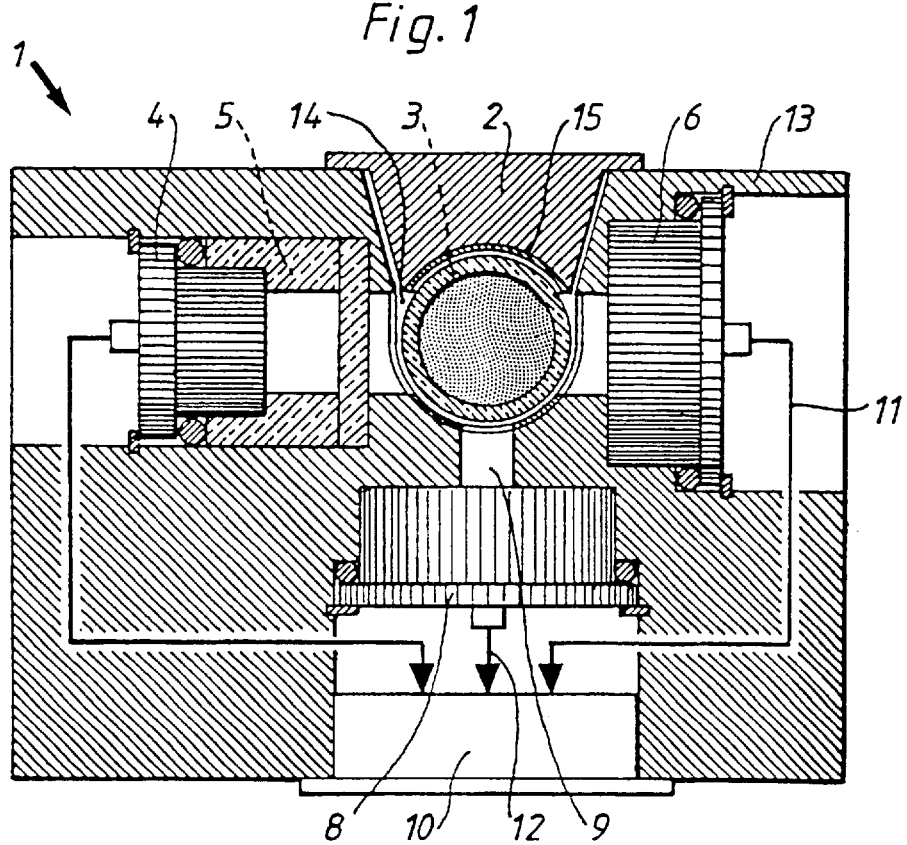
FIG. 1 is a front, elevational, schematic, cross-sectional view of an embodiment of the present invention.

Referring to the drawings, FIG. 1 discloses a schematic cross-sectional view of a first embodiment of the present invention. The blood sensor 1 comprises a cavity 14 closed by a lid 2. The cavity is adapted to receive a flow cuvette 3, which is shown in place in FIG. 1.

The flow cuvette can be inserted and removed from the cavity 14 through the opening provided by the lid 2. The flow cuvette may have a circular cross-section, as is shown in the drawings or may have any desired cross-section, such as rectangular. The cuvette is preferably made of hard transparent plastic material, and is designed to have the same cross-sectional area over the entire length.

The flow cuvette may be included in a tube set for an extracorporeal blood circuit, such as a tube set intended for hemodialysis, hemofiltration, hemodiafiltration, plasmapheresis, blood component separation, oxygenation or similar treatments. Preferably, the tube set and the cuvette comprises whole blood from a mammal having a red blood cell concentration to be measured by the blood sensor according to the present invention.

The blood sensor 1 further comprises a light emitting diode (LED) 4 mounted in a housing 5 for emitting light at a predetermined cone angle of approximately 120°. LED 4 emits light of a predetermined wavelength, which preferably is at an isobestic point for which the influence of oxygen saturation is at a minimum. The wavelength preferred according to the present invention is 805 nm. Alternative wavelength may be 548 and 586 nm.

Opposite the LED 4 there is arranged a first photo diode 6, referred to below as the transmitted light diode, for receiving light from the LED 4 transmitted through the flow cuvette essentially along a diameter of the cuvette, extending from the LED towards the diode 6. Transmitted light diode 6 provides a signal indicative of the transmitted light intensity. The diode 6 is arranged to receive collimated light passing through a straight transmission path 7, which extends from the LED 4 towards the diode 6.

Perpendicular to the transmission path 7, there is arranged a second photo diode 8, referred to below as the scattered light diode, for receiving light emitted by LED 4 and side scattered essentially perpendicular to the transmission path by the contents of the flow cuvette. Scattered light diode 8 receives light through an opening 9 to minimise any undesired direct light from the LED 4. Scattered light diode 8 emits a signal indicative of the side scattered light scattered over 90°.

The signals emitted by transmitted light diode 6 and scattered light diode 8 are fed to a computing unit 10 by means of wires 11 and 12. The computing unit may be a central computing unit arranged in the machine, in which the blood sensor 1 is connected, or may be arranged in the blood sensor itself as indicated in FIG. 1.

The computing unit is arranged to calculate a ratio signal by dividing the scattered light signal provided by the scattered light diode 8 and the transmitted light signal provided by the transmitted light diode 6 to provide an optical ratio signal according to the present invention. The computing unit may also provide drive signals to the LED 4 to have full control of the operation of the blood sensor. The drive signals may be pulsed signals to reduce the influence of background light on the recorded scattered and transmitted light signals provided by the light diodes, 8 and 6, respectively.

The different components of the blood sensor 1 are mounted in a housing 13 which is provided with openings and recesses and shoulders as required to provide support for the LED 4 and the photo diodes, 6 and 8. As is shown in FIG. 1, these components may be mounted by means of O-rings.

The interior surfaces of the cavity 14 may be covered by a light absorbing material, such as black painting 15, as shown in FIG. 1, in order to reduce the risk that the transmitted and scattered light signals become distorted by reflections in the cavity.

Figure 2:
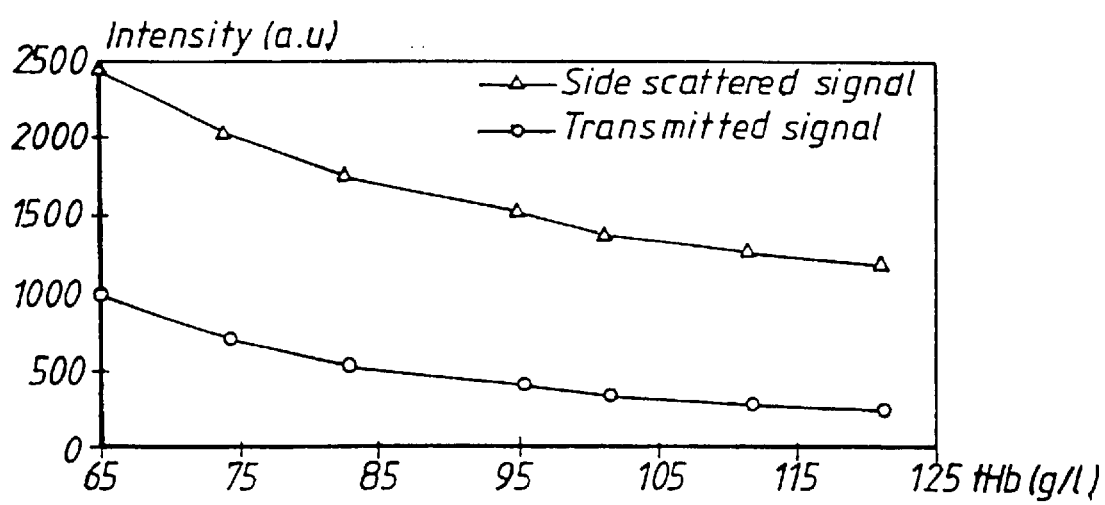
FIG. 2 is a graphical representation of the scattered and transmitted signals versus total hemoglobin recorded by the embodiment of FIG. 1.

The signals emitted by the transmitted light diode 6 and the scattered light diode 8 are shown in FIG. 2 versus total hemoglobin in gram/liter for bovine blood at a flow rate of 300 ml/min. As expected, they both have a typical exponential decay with increasing total hemoglobin, which substantially corresponds to the concentration of red blood cells.

Figure 3:
FIG. 3 is a graphical representation of the ratio signal between the scattered signal and transmitted signal versus total hemoglobin.

As is shown in FIG. 3, the ratio signal has, however, a substantially linear relationship with total hemoglobin. This linear relationship is a highly desired property, since it provides a robust signal to be used for measuring total hemoglobin or concentration of red blood cells.

Figure 4:
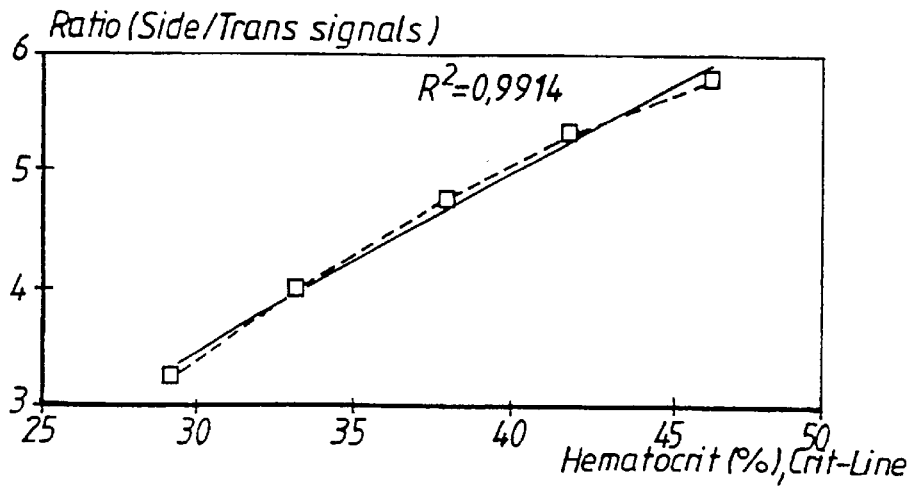
FIG. 4 is a graphical representation of the relationship between the ratio signal recorded by the embodiment of FIG. 1 versus hematocrit as measured by a reference instrument.

FIG. 4 shows the ratio signal compared with a signal from an accurate reference hematocrit sensor, provided by In-Line Diagnostics Corporation under the trademark CRIT-LINE. As clearly appears from FIG. 4, the ratio signal according to the present invention is substantially proportional to the hematocrit as measured by the reference instrument, with a correlation coefficient close to unity (0.991). The measurements were performed with bovine blood at a blood flow rate of 300 ml/min.

Figure 5:
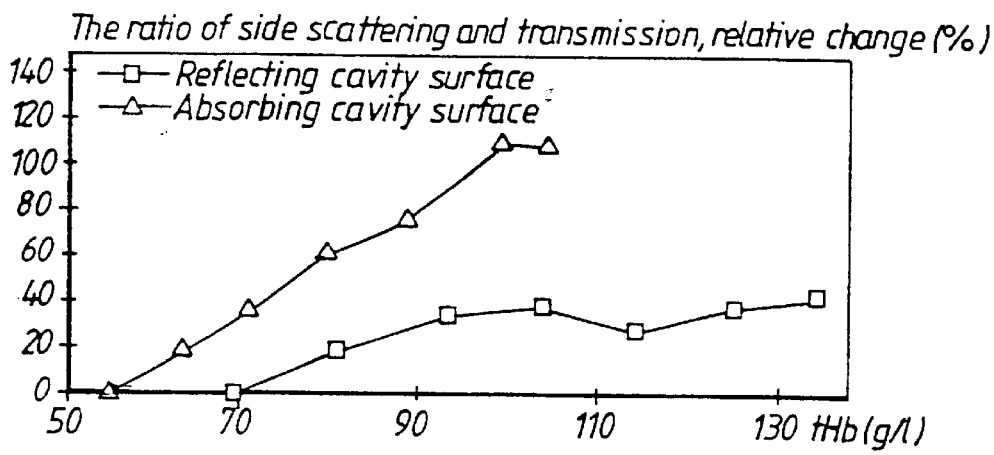
FIG. 5 is a graphical representation of the relative change of the signals of the embodiment according to FIG. 1, with and without light absorption painting.

FIG. 5 shows the ratio signal according to the present invention with reflecting cavity surfaces and with absorbing cavity surfaces, the surfaces being painted with light absorbing color or coating. As clearly appears from FIG. 5, the ratio signal has a larger slope when the reflections in the cavity have been eliminated. Moreover, the linearity at high total hemoglobin is better with absorbing surfaces. The reason for this is probably that the transmitted signal is very low at high total hemoglobin concentrations and that background light is reflected to the transmitted light diode 6 and disturbs the correct signal. Also the scattered light signal may be corrupted by reflections.

Figure 6:
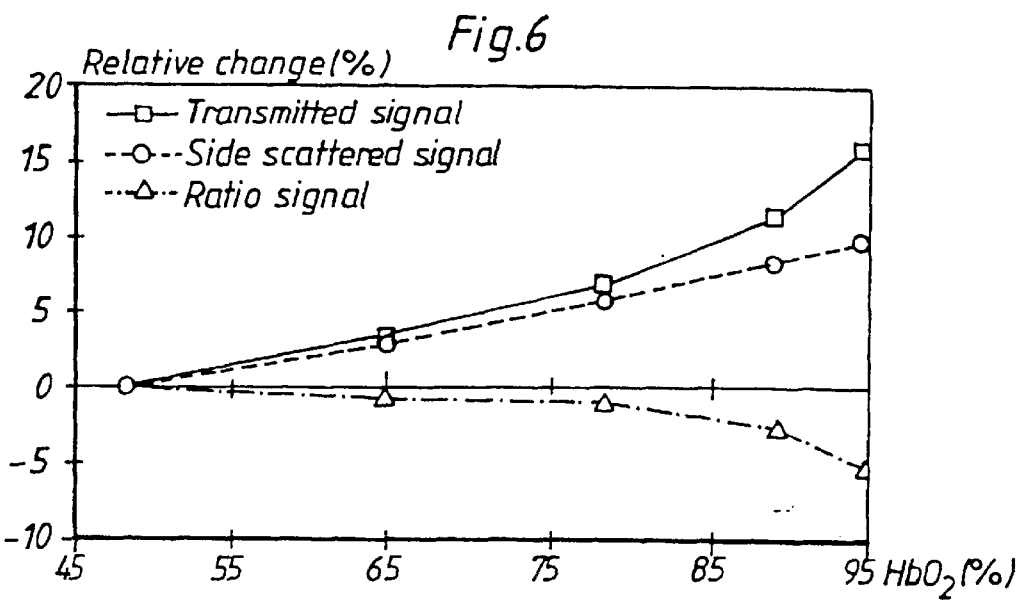
FIG. 6 is a graphical representation of the relative change of the transmitted signal, scattered signal and ratio signal versus blood oxygenation.

FIG. 6 shows the relative change of the transmitted signal, the side scattered signal and the ratio signal when the oxygenation level of the blood is increased from 50% to 95%. Both the transmitted and the scattered signals have a high relative change, while the ratio signal has a low dependency, making it ideal for measurement at varying oxygenation levels. The indicated change takes place in spite of the fact that the peak wavelength of the light used is centered at the isobestic point, in this case 805 nm, for which the changes due to the oxygenation level are minimal.

Figure 7:
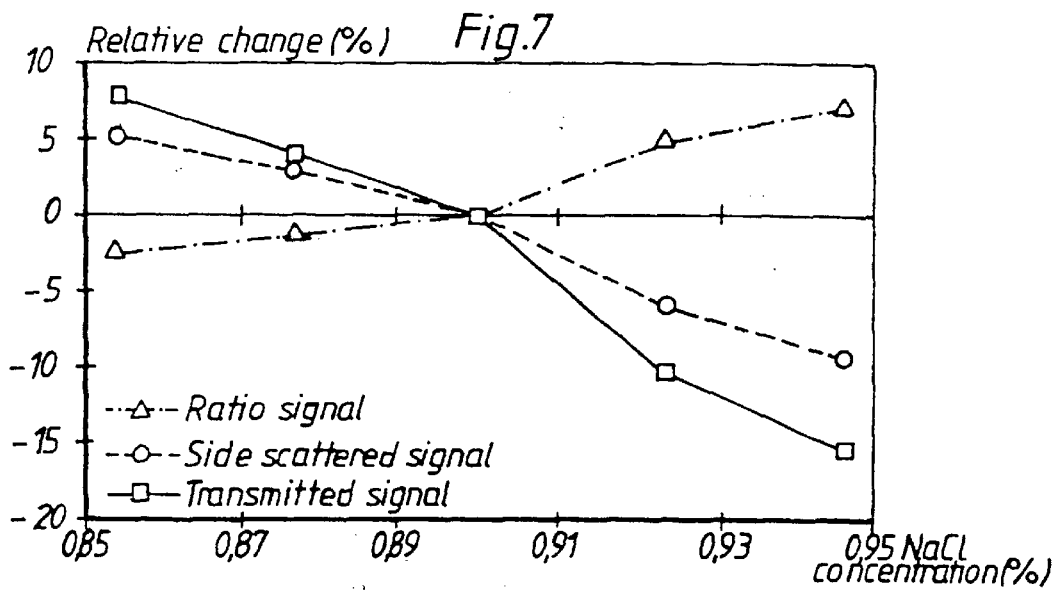
FIG. 7 is a graphical representation of the relative change of the transmitted signal, scattered signal and ratio signal versus osmolarity represented by sodium chloride concentration.

FIG. 7 discloses the relative change of the transmitted signal, the side scattered signal and the ratio signal versus different sodium chloride concentrations, around the physiological level of 0.90%, which is the reference point for the diagram. The diagram suggests the dependency of the signals to different osmolarities of the fluid. The osmolarity affects the size and shape of the red blood cells. As appears from FIG. 7, the ratio signal varies less than the other signals at varying osmolarity.

Figure 8A:
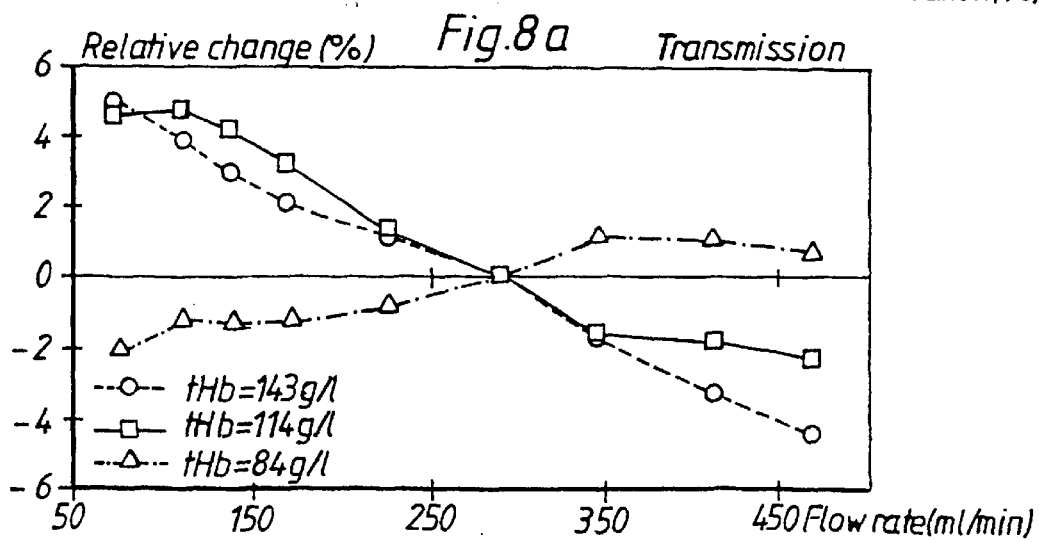
FIG. 8a is a graphical representation of the relative change of the transmitted signal, scattered signal and ratio signal versus blood flow rate.
Figure 8B:
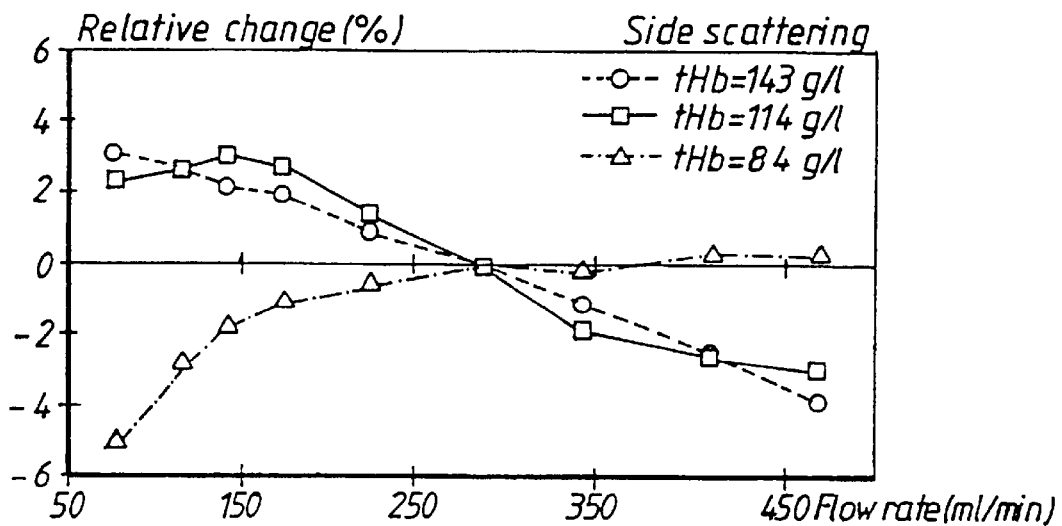
FIG. 8b is a graphical representation of the relative change of the transmitted signal, scattered signal and ration signal versus blood flow rate.
Figure 8C:
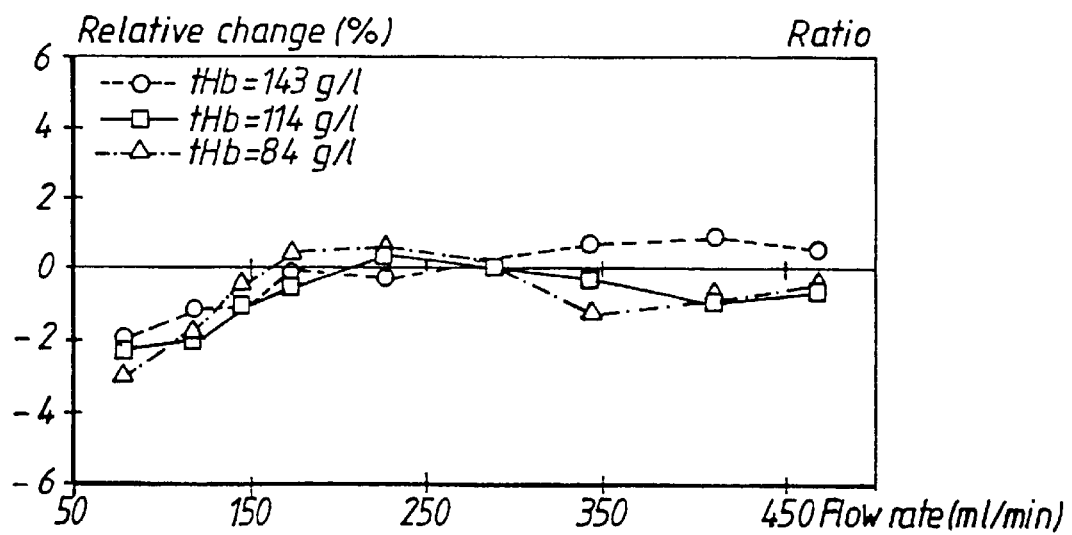
FIG. 8c is a graphical representation of the relative change of the transmitted signal, scattered signal and ration signal versus blood flow rate.

Finally, FIGS. 8a, 8b and 8c indicates the relative change of the three signals for different flow rates between 50 ml/min to 450 ml/min, which are the flow rates commonly used during extracorporeal blood treatment, and at different total hemoglobin. The flow rate is expected to influence the red blood cells, mainly with respect to the shape and alignment of the cells.

Significant influences of the flow rate can be observed on the measured signals, which in turn depend on the concentration of red blood cells, represented by the total concentration of hemoglobin. The ratio signal is less influenced by the flow rate and not significantly affected by the total hemoglobin.

The beneficial linearity of the ratio signal with total hemoglobin has been found for light scattered substantially 90° in relation to the transmission signal. Since both signals are exponential, the ratio is linear only if the exponents are substantially the same. It has been found, according to the present invention, that this occurs only when the light is scattered over substantially 90°. However, substantially the same effect appears at light scattered between 70° and 110°, more specifically between 80° and 100°.

The optical blood sensor described above has been demonstrated to be useful for providing a ratio signal which is linearly related to hematocrit, total hemoglobin or the concentration of red blood cells. The blood sensor may be used in connection with extracorporeal blood treatment to detect the concentration of blood or measure blood volume during, for example, hemodialysis.

The blood concentration signal obtained from the blood sensor is robust and only slightly affected by oxygenation level, osmolarity and blood flow rate. Moreover, the accuracy is relatively high. These properties make the blood sensor ideal for use as a feedback control instrument for controlling the blood volume by feedback during treatment.

The blood sensor may alternatively be used as an instrument for alerting the dialysis care personnel about an imminent hazardous condition, like hypotension.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for analyzing the concentration of red blood cells in a flow of blood comprising flowing said blood through a cuvette, directing a light along a direct transmission path through said flow of blood in said cuvette, measuring light transmitted through said flow of blood along said direct transmission path to obtain a transmitted signal, measuring scattered light at a predetermined angle with respect to said direct transmission path to obtain a scattered signal, and providing a ratio signal comprising the ratio between said scattered signal and said transmitted signal.

2. The method of claim 1 wherein said predetermined angle is about 90°.

3. The method of claim 1 wherein said predetermined angle is between 70° and 110°.

4. The method of claim 3 wherein said predetermined angle is between 80° and 100°.

5. The method of claim 1 including directing said light from a light emitting member, measuring said light transmitted along said direct transmission path by means of a first light sensitive member, and measuring said scattered light by means of a second light sensitive member.

6. The method of claim 5 including surrounding at least a portion of said cuvette with light absorbing material in order to increase the sensitivity of said ratio signal.

7. The method of claim 6 including emitting light having a restricted emission angle by means of said light emitting member.

8. The method of claim 6 including activating said light emitting member in a pulsed mode.

9. Apparatus for analyzing the concentration of red blood cells in a flow of blood comprising a cuvette for said flow of blood, a light emitting member for directing a light along a direct transmission path through said flow of blood in said cuvette, a first light sensitive member for measuring light transmitted through said flow of blood along said direct transmission path to obtain a transmitted signal, a second light sensitive member for measuring scattered light at a predetermined angle with respect to said direct transmission path to obtain a scattered signal, and calculation means for providing a ratio signal comprising the ratio between said scattered signal and said transmitted signal.

10. The apparatus of claim 9 wherein said predetermined angle is about 90°.

11. The apparatus of claim 9 wherein said predetermined angle is between 70° and 110°.

12. The apparatus of claim 11 wherein said predetermined angle is between 80° and 100°.

13. The apparatus of claim 9 including light absorbing material surrounding at least a portion of said cuvette.

14. The apparatus of claim 13 wherein said light emitting member has a restricted emission angle.

15. The apparatus of claim 9 wherein said light emitting member is driven in a pulsed mode.

* * * * *